United States Patent

Bhatnagar et al.

Patent Number: 5,276,167
Date of Patent: Jan. 4, 1994

[54] PROCESS FOR THE PREPARATION OF THE LACTONE OF 1R, CIS 2,2-DIMETHYL-3-FORMYL-CYCLOPROPANE-1-CARBOXYLIC ACID

[75] Inventors: Neerja Bhatnagar, Savignv-sur-Orge; Francois Brion, Gagny; Colette Colladant, Rosny Sous Bois, all of France

[73] Assignee: Roussel Uclaf, France

[21] Appl. No.: 964,500

[22] Filed: Oct. 21, 1992

[30] Foreign Application Priority Data

Nov. 8, 1991 [FR] France .................. 91 13776

[51] Int. Cl.$^5$ ............................ C07D 307/00
[52] U.S. Cl. ...................... 549/302; 549/313
[58] Field of Search .................. 549/313, 302

[56] References Cited

U.S. PATENT DOCUMENTS 4,014,918  3/1977  Martel ................. 549/313

FOREIGN PATENT DOCUMENTS 1580474  9/1969  France .
2396006  1/1979  France .

OTHER PUBLICATIONS

Copy of Agr. Biol. Chem., vol. 29, No. 8, pp. 784-786 (1965) Copy of European Search Report (4 pages).

*Primary Examiner*—C. Warren Ivy
*Assistant Examiner*—Raymond Covington
*Attorney, Agent, or Firm*—Bierman and Muserlian

[57] ABSTRACT

A process for preparation of a compound of the formula

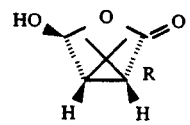

14 Claims, No Drawings

PROCESS FOR THE PREPARATION OF THE LACTONE OF 1R, CIS 2,2-DIMETHYL-3-FORMYL-CYCLOPROPANE-1-CARBOXYLIC ACID

STATE OF THE ART

The lactone of formula I is described in U.S. Pat. No. 4,014,918 and is an important intermediate for the synthesis of well known esters having an excellent insecticidal activity as described in French Patent No. 2,396,006.

OBJECTS OF THE INVENTION

It is an object of the invention to provide an improved process for the preparation of the lactone of 1R, cis 2,2-dimethyl-3-formyl-cyclopropane-1-carboxylic acid and novel intermediates.

These and other objects and advantages of the invention will become obvious from the following detailed description.

THE INVENTION

The novel process of the invention for preparation of a compound of the formula

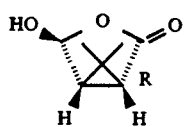

I comprises reacting a compound of the formula

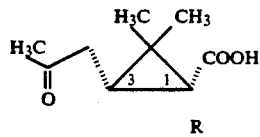

II of 1R,cis configuration with at least 2 equivalents of a halogen selected from the group consisting of chlorine, bromine and iodine to obtain either a compound of the formula

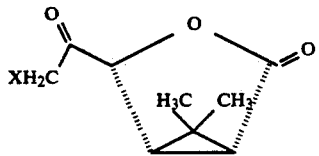

III₁ or a compound of the formula

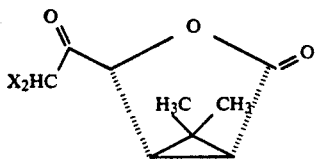

III₂ or a compound of the formula

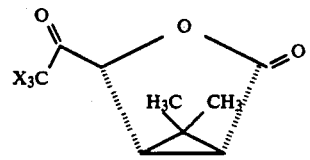

III₃ in which X is a halogen as defined above optionally in a mixture with a compound of the formula

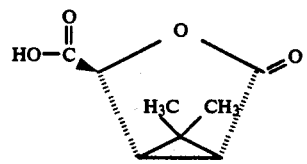

IV optionally continuing the halogenation of the compound of formula III$_1$ or III$_2$ with excess halogen as defined above to obtain the compound of formula III$_3$, reacting the compound of formula III$_3$ optionally in the form of a mixture with a compound of formula IV with a basic agent to obtain the compound of formula IV, existing in that case in the reaction medium in the form of its salt corresponding to the basic agent used, or of that of the open form

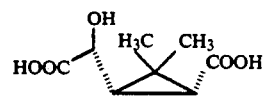

IV' optionally acidify the reaction medium to obtain the acid of formula IV or IV' and reacting the said acid or the said salt with an oxidizing agent to obtain the compound of formula I.

Preferably, the compound of formula II is reacted with at least 4 equivalents of the halogen to obtain the compound of formula III$_3$ in admixture with the compound of formula IV which mixture is then treated to form the compound of formula I. The halogen is preferably chlorine or bromine.

In a preferred process of the invention, the halogenation is carried out at ambient temperature in a halogenated organic solvent which can be for example methylene chloride, chloroform, carbon tetrachloride, dichloroethane, or a mixture of these solvents, or also an organic ester such as ethyl acetate. The crude reaction medium deriving from the halogenation is treated with a basic agent, for example an alkali metal or alkaline earth metal hydroxide or carbonate before isolating the halogenated compound and the basic agent with which the compound of formula III$_3$ is treated is chosen from the group consisting of alkali metal, alkaline earth metal and magnesium hydroxides and carbonates and is used in the presence of water. The salt of the compound of formula IV' forms preferably if the basic agent is used in excess.

The acid that is optionally used to obtain the compound of formula IV or IV' can be a standard organic or mineral acid such as hydrochloric acid or sulfuric acid.

The oxidizing agent with which the compound of formula IV or IV' or its salt is treated can be preferably chosen from the group consisting of hypohalous acids, alkali metal, alkaline earth metal and magnesium hypohalites, potassium permanganate, chromic acid, periodic acid and the alkali metal bismuthates or manganese dioxide or a perborate. A hypohalous acid, preferably hypochlorous acid, is more particularly preferred.

In the preferred conditions for implementing the process, the hypohalous acid used as an oxidizing agent is obtained in situ from an alkali metal, alkaline earth metal or magnesium hypohalite placed in acid medium. Hypochlorous acid is obtained in situ from sodium hypochlorite.

The acid used to liberate the hypochlorous acid is preferably chosen from the group consisting of lower alkanoic acids such as acetic acid or propionic acid as well as solutions of phosphates, borates and acetates of appropriate pH.

The starting compound of formula II is known for example from Agr. Biol. Chem., Vol. 29, No. 8, p. 784 (1965).

The action of the halogen on the compound of formula II leads intermediately to an open form of the lactone of formula $III_1$, $III_2$ or $III_3$ which leads to said lactone by the action of a basic agent in aqueous medium. It should be noted that a certain quantity of the acid-lactone of formula IV can also form at the same time as the lactone and more particularly as the lactone of formula $III_2$ and $III_3$.

Therefore the reaction in its totality may be illustrated as follows:

The compound of formula IV as well as its open form IV' and their salts with bases are also compounds and constitute one of the subjects of a patent application filed on the same day as the present application by the applicant and also entitled: "New preparation process for the lactone of 1R,cis 2,2-dimethyl-3-formylcyclopropane-1-carboxylic acid and intermediates".

In the following examples, there are described several preferred embodiments to illustrate the invention. However, it is to be understood that the invention is to intended to be limited to the specific embodiments.

EXAMPLE 1

(1R-(1α, 4β, 5 α))-6,6-dimethyl-4-(tribromo-acetyl)-3-oxabicyclo [3.1.0]hexan-2-one and (1S-(1α, 2β, 5 α)-6,6-dimethyl-4-oxo-3-oxabicyclo [3.1.0]hexane-2-carboxylic acid 0.51 g of 1R,cis 2,2-dimethyl-3-(2-oxo-propyl)-cyclopropane -1-carboxylic acid, 10 ml of chloroform and 10 ml of carbon tetrachloride were mixed together under an inert gas atmosphere and after the mixture was cooled to +5° C., 0.7 ml of bromine (4.5 equivalents) was added slowly. The mixture was stirred for 18 hours at ambient temperature and 15 ml of ice-cooled water were introduced. The mixture was stirred for 1 hour and then 2.12 g of potassium carbonate were added and

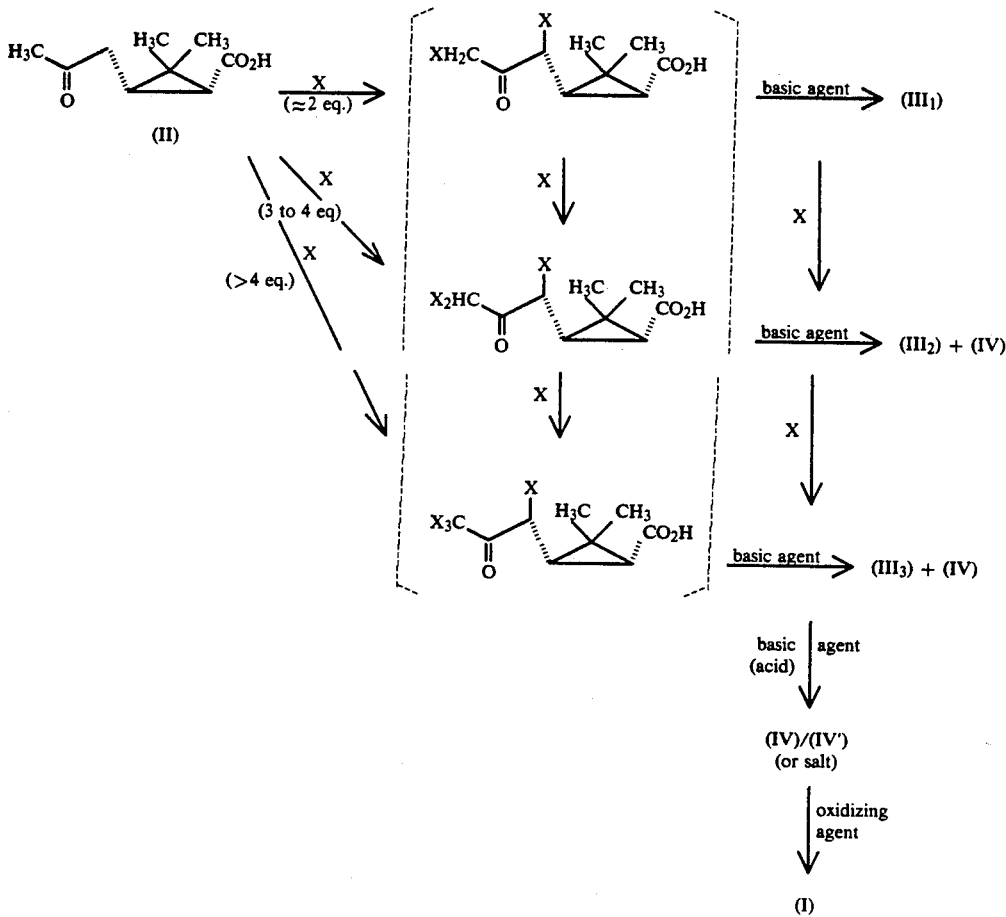

The new industrial intermediates which are necessary for the implementation of the process of the invention are the compounds of formula $III_1$, $III_2$ and $III_3$ as defined above.

the mixture was stirred for 1 hour and then poured into 15 ml of water. Extraction took place with methylene chloride and the organic phase was dried and evaporated to dryness. The crude product was crystallized from a methylene chloride isopropyl ether mixture to obtain 0.222 g of the expected tribrominated derivative melting at 188° to 190° C. Thin layer chromatography of the reaction medium revealed the presence of the corresponding dibrominated derivative, along with the tribrominated derivative. The aqueous phase was acidified to a pH 1 by the addition of 2N hydrochloric acid and was extracted with a mixture of ethyl acetate and methanol (9-1). The organic phase was dried and the solvent was evaporated. The residue was chromatographed on silica eluting with the ethyl acetate - methanol mixture (75 /25) to obtain 0.2 g of the lactone of 2,2-dimethyl-3-hydroxycarboxy-methyl-cyclopropane-1-carboxylic acid (or 1S 1α, 2β, 5α)) -6,6-dimethyl-4-oxo-3-oxabicyclo [3.1.0] hexane-2-carboxylic acid).

NMR spectrum of the tribrominated derivative (CDCl$_3$—250 MHz): 1.24 and 1.30: CH$_3$ twin; 2.17 (d, J=6) and 2.31 (d, J=6); H$_1$ and H$_3$ 5.56 (s)—O—CH—CO—

EXAMPLE 2

(1R-(1 α, 4 β, 5 α)-6.6-dimethyl-4-(dibromoacetyl)-3-oxabicyclo [3.1 0] hexan-2-one and (1S-(1 α, 2 β, 5 α))-6.6-dimethyl-4-oxo -3-oxabicyclo 3.1.01 hexane-2-carboxylic acid 0.34 g of 1R, cis 2,2-dimethyl-3-(2-oxo propyl)-cyclopropane-1-carboxylic acid, 6 ml of chloroform and 6 ml of carbon tetrachloride were mixed together under an inert gas atmosphere and the mixture was cooled to +5° C. 0.4 ml of bromine (4 equivalents) were added slowly and the mixture was stirred for 6 hours at +5° C., then for 16 hours at ambient temperature. After cooling to +5° C., 10 ml of ice-cooled water were added, followed by stirring for 1 hour. Then, 1.5 g of potassium carbonate were added and the mixture was stirred for 1 hour and poured into 15 ml of water. The mixture was extracted with methylene chloride. The organic phase was dried and the solvent was evaporated off to obtain 0.22 g of the expected product containing traces of the corresponding tribrominated derivative.

The aqueous phase was acidified to a pH of 1 by the addition of hydrochloric acid and extracted with ethyl acetate. The organic phase was dried and evaporated to dryness. The residue was chromatographed on silica eluting with a methylene chloride -acetic acid mixture (9/1) to obtain 0.1 g of the lactone of 2,2-dimethyl -3-hydroxy-carboxy-methyl-cyclopropane-1-carboxylic acid (or 1S -(1 α, 2 β, 5 α))-6,6-dimethyl-4-oxo-3-oxabicyclo [3.1.0] hexane-2-carboxylic acid).

NMR spectrum of the dibrominted derivative (CDCl$_3$-250 MHz): 1.24 and 1.25: CH$_3$ twin; 2.07 (d, J=6) and 2.41 (d, J=6): H$_1$ and H$_3$; 4.90 (s): —CO—CH—O—; 6.38(s): =C—CHX$_2$.

EXAMPLE 3

(1R-(1 α, 4 β, 5 α))-4-(bromoacetyl)-6,6-dimethyl-3-oxabicyclo [3.1.0] hexan-2-one 0.54 g of 1R,cis 2,2-dimethyl-3-(2-oxo-propyl)-cyclopropane-1-carboxylic acid, 5 ml of carbon tetrachloride and 10 ml of methylene chloride were mixed together under an inert gas atmosphere and after cooling to 2° to +5° C., 0.32 ml of bromine (2 equivalents) were added slowly. The mixture was stirred at ambient temperature for 9? minutes and then 10 ml of water were added. The mixture was stirred for 15 minutes and after cooling to 5° C., 1.32 g of potassium carbonate were added. The mixture was stirred for 1 hour at +5° C. and was poured into 20 ml of water. Extraction took place with methylene chloride and the organic phase was dried. The solvent was evaporated off and then the residue was chromatographed on silica, eluting with an ethyl acetate-cyclohexane mixture (7/3) to obtain 0.51 g of the expected product.

NMR Spectrum (CDCl$_3$- 250 MHz): 1.23 (s): CH$_3$ twin; 2.05 (d, J=6) and 2.34 (d, J=6); H$_1$ and H$_3$ (cis. cyclopropyls; 4.09 (d, J$_{AB}$=12.5) and 4.23 (d, J$_{AB}$12.5): —CO—CH$_2$X; 4.68 (s) —CO—CH—O—CO.

EXAMPLE 4

(1R-(1 α, 4 β, 5 α))-4-(dibromoacetyl)-6,6-dimethyl-3-oxabicyclo (3.1.0) hexan-2-one 0.125 g of (1R-(1 α, 4 β, 5α))-4-(bromoacetyl)-6,6-dimethyl-3-oxabicyclo [3.1.0] hexan-2-one of Example 3 were mixed under an inert ga atmosphere with 1 ml of methylene chloride and 1 ml of chloroform. 50 μl of bromine were added slowly at +25° to 30° C. and the mixture was stirred for 48 hours at ambient temperature. Water was added, followed by decanting and extracting with methylene chloride. The organic phase was dried and the solvent was evaporated under reduced pressure to obtain 0.199 g of the crude expected product in the form of an oil.

NMR Spectrum (CDCl$_3$- 250 MHz): 1.24 (s): CH$_3$ twin; 2.08 (d) and 2.41 (d); H$_1$ and H$_3$; 4.90 (s): —CO—CH—O—; 6.38 (s) —CO—CHX$_2$.

EXAMPLE 5

Lactone of 1R,cis 2,2-dimethyl 3-hydroxy-carboxy-methyl-cyclo-propane-1-carboxylic acid or (1S-(1 α, 2 β, 5 α,))-6-6-dimethyl -4-oxo-3-oxabicyclo [3.1.0]hexane-2-carboxylic acid 0.5 g of the tribrominated product of Example 1 were dissolved under an inert gas atmosphere in approximately 5 ml of methylene chloride and 20 ml of water were added. Then, 3.4 g of potassium carbonate were added and the mixture was stirred at ambient temperature for 18 hours. Then, it was acidified to a pH of 1 by the addition of 2N hydrochloric acid. Extraction took place with an ethyl acetate and methanol mixture (9/1) and the organic phase was dried and the solvent was evaporated to obtain 0.2 g of the crude expected product which was washed with cold ethyl acetate for a melting point of=177° C. and a specific rotation of [α]$^{20}_D$= −100° (c=1% in DMF).

NMR spectrum (CDCl$_3$- 250 MHz): 1.20 (s) and 1.26 (s); CH$_3$ twin; 2.09 (d, J=6) and 2.38 (m): H$_1$ and H$_3$/cis cyclopropyls; 5.12 (d, J=6): —CH—O—.

EXAMPLE 6

Lactone of 1R,cis 2,2-dimethyl-3-formyl-cyclopropane-1-carboxylic acid or (1S-(1 α, 2 β, 5 α))-6,6-dimethyl-4-oxo-3-oxa -bicyclo [3.1.0.] hexan-2-ol 0.8 g of the acid of Example 5 were mixed with 16 ml of water and 6.3 ml of 2N sodium hydroxide and 2.4 ml of an aqueous solution of sodium hypochlorite, then a few drops of acetic acid were added at ambient temperature. The mixture was stirred for 1 hour and then an aqueous solution of sodium thiosulfate was added until the oxidizing power disappeared. Then, concentrated hydrochloric acid was added until a pH of approximately 2.5 was reached and finally 10 g of ammonium sulfate were added. Extraction took place with methylene chloride and the organic phase was dried and evaporated to dryness. The residue was crystallized from toluene to obtain 0.2 g of the expected product melting at 114.5° C. and having a specific rotation of $[\alpha]^{20}_D = -101°$ (c=1% in DMF).

Various modifications of the process of the invention may be made without departing from the spirit or scope thereof and it is to be understood that the invention is intended to be limited only as defined in the appended claims.

What we claim is:

1. A process for preparation of a compound of the formula

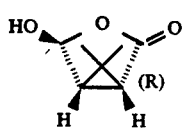

I comprising reacting a compound of the formula

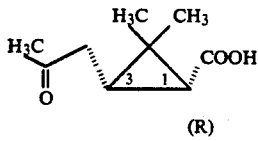

II of 1R,cis configuration with at least 2 equivalents of a halogen selected from the group consisting of chlorine, bromine and iodine to obtain either a compound of the formula

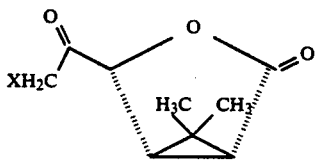

III$_1$ or a compound of the formula

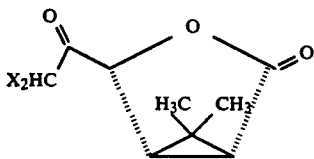

III$_2$ or a compound of the formula

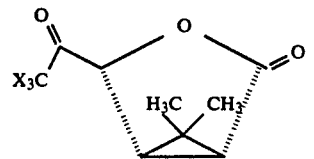

III$_3$ in which X is halogen as defined above optionally in a mixture with a compound of the formula

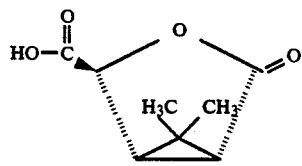

IV optionally continuing the halogenation of the compound of formula III$_1$ or III$_2$ with excess halogen as defined above to obtain the compound of formula III$_3$, reacting the compound of formula III$_3$ optionally in the form of a mixture with a compound of formula IV with a basic agent to obtain the compound of formula IV, existing in that case in the reaction medium in the form of its salt corresponding to the basic agent used, or of that of the open form

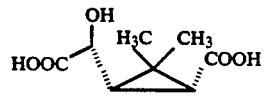

IV' optionally acidifying the reaction medium to obtain the acid of formula IV or IV' and reacting the said acid or the said salt with an oxidizing agent to obtain the compound of formula I.

2. The process of claim 1 wherein the compound of formula II of 1R,cis configuration is reacted with at least 4 equivalents of halogen to obtain the compound of formula III$_3$, in a mixture with a compound of formula IV, then reacting said mixture as indicated in claim 1 to obtain the compound of formula I.

3. The process of claim 1 wherein the halogen is chlorine or bromine.

4. The process of claim 1 wherein the reaction is effected in a halogenated organic solvent or an organic ester.

5. The process of claim 1 wherein the crude reaction medium of the halogenation is treated with a basic agent selected from the group consisting of alkali metal and alkaline earth metal hydroxides and carbonates before isolating the halogenated compound.

6. The process of claim 1 wherein the basic agent is selected from the group consisting of alkali metal, alkaline earth metal and magnesium hydroxides and carbonates in the presence of water.

7. The process of claim 1 wherein the oxidizing agent is selected from the group consisting of hypohalogenous acids, alkali metal, alkaline earth metal and magnesium hypohalites, potassium permanganate, chromic anhydride, periodic acid and the alkali metal bismuthates.

8. The process of claim 1 wherein the oxidizing agent is a hypohalogenous acid.

9. The process of claim 8 wherein the hypohalogenous acid is obtained in situ from an alkali metal, alkaline earth metal or magnesium hypohalite in acid medium.

10. The process of claim 9 wherein the oxidizing agent is hypochlorous acid.

11. The process of claim 9 wherein the hypochlorous acid is obtained in situ from sodium hypochlorite placed in acid medium.

12. The process of claim 9 wherein the acid is selected from the group consisting of lower alkanoic acids and solutions of phosphates, borates and acetates of appropriate pH.
13. The process of claim 12 wherein the acid is acetic acid or propionic acid.
14. A compound selected from the group consisting of formula
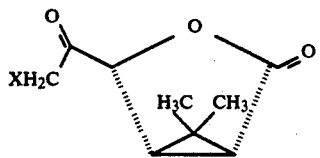 III₁
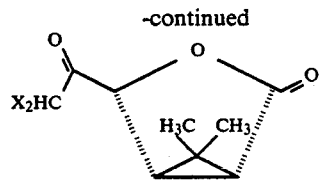 III₂
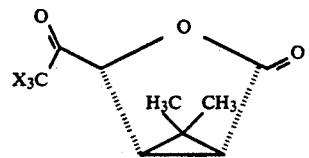 III₃
wherein X is halogen.
* * * * *